(12) United States Patent
An et al.

(10) Patent No.: US 9,081,890 B2
(45) Date of Patent: Jul. 14, 2015

(54) REHABILITATION TRAINING SYSTEM AND METHOD

(71) Applicant: DAEGU GYEONGBUK INSTITUTE OF SCIENCE & TECHNOLOGY, Daegu (KR)

(72) Inventors: Jinung An, Daegu (KR); Sang Hyeon Jin, Daegu (KR); Seung Hyun Lee, Daegu (KR); Jeon Il Moon, Daegu (KR); Berdakh Abibullaev, Daegu (KR); Jae Hyun Ahn, Daegu (KR); Gwang Hee Jang, Daegu (KR)

(73) Assignee: Daegu Gyeongbyk Institute of Science and Technology, Daegu (KR)

( * ) Notice: Subject to any disclaimer, the term of this patent is extended or adjusted under 35 U.S.C. 154(b) by 1 day.

(21) Appl. No.: 13/914,826

(22) Filed: Jun. 11, 2013

(65) Prior Publication Data

US 2014/0135873 A1    May 15, 2014

(30) Foreign Application Priority Data

Nov. 13, 2012    (KR) .......................... 10-2012-0128419

(51) Int. Cl.
*G06F 19/00* (2011.01)
(52) U.S. Cl.
CPC .................................. *G06F 19/3481* (2013.01)

(58) Field of Classification Search
None
See application file for complete search history.

(56) References Cited

U.S. PATENT DOCUMENTS

| 5,410,472 A | * | 4/1995 | Anderson | 482/9 |
| 2005/0283205 A1 | | 12/2005 | Lee et al. | |
| 2006/0079817 A1 | * | 4/2006 | Dewald et al. | 601/5 |
| 2009/0233769 A1 | * | 9/2009 | Pryor | 482/8 |

FOREIGN PATENT DOCUMENTS

| KR | 10-2004-0051264 A | 6/2004 |
| KR | 10-0624424 B1 | 9/2006 |
| KR | 10-0822483 B1 | 4/2008 |
| KR | 2011-0118879 A | 11/2011 |

* cited by examiner

*Primary Examiner* — Brian T Gedeon
*Assistant Examiner* — Ankit Tejani
(74) *Attorney, Agent, or Firm* — Sughrue Mion, PLLC

(57) ABSTRACT

Provided are a rehabilitation training system and method that provide active rehabilitation training to a patient requiring rehabilitation treatment. The rehabilitation training system and method provide rehabilitation-related information to the patient to provoke a rehabilitation intent of the patient, and continuously measure a biological signal of the patient to monitor a state of the patient, thereby providing active rehabilitation training suitable for the state of the patient.

7 Claims, 4 Drawing Sheets

REHABILITATION TRAINING SYSTEM AND METHOD

CROSS-REFERENCE TO RELATED APPLICATIONS

This application claims priority under 35 U.S.C. §119 to Korean Patent Application No. 10-2012-0128419, filed on Nov. 13, 2012, the disclosure of which is incorporated herein by reference in its entirety.

TECHNICAL FIELD

The present invention relates to a rehabilitation training system and method that provide rehabilitation training to a central nervous system damaged patent due to a brain damage or a spinal damage, a musculoskeletal disease patient, a sports rehabilitation-requiring patient, or the like, and more particularly, to a rehabilitation training system and method that enable an active user to be rehabilitated through training.

BACKGROUND

Rehabilitation treatment denotes a series of measure process which is performed for functionally recovering a damaged part or function weakened part of a patient whose body part is damaged by a disease, an accident, a disaster, or the like, or who undergoes severe surgery and then is in a convalescent stage.

Conventional rehabilitation treatment is performed by a therapist, a robot, or an electrical simulator, or the like, and thus is generally provided to patients unilaterally and passively.

For this reason, from the cerebral nerve perspective, since complete sensor-motor looped rehabilitation is not made, the conventional rehabilitation treatment can be considered as a method applicable to acute patients or subacute patients, but is not suitable for chronic patients undergoing a rehabilitation plateau that is a period for which a rehabilitation effect is no longer improved by passive rehabilitation and a current rehabilitation state is maintained as-is.

SUMMARY

Accordingly, the present invention provides a rehabilitation training system and method that present rehabilitation training appropriate for a patient as sensory information such as a visual sense or the like, measure a biological signal associated with a central nervous system, a musculoskeletal system, a sensory system, or the like based on the sensory information to estimate a patient state, and enable the patient itself to separately or simultaneously enhance a plasticity of brain, musculoskeletal recovery, and an exercise-enabling range through sensory-motor looped rehabilitation by using methods for providing a stimulation or exercise suitable for the patient state.

In one general aspect, a rehabilitation training system includes: a rehabilitation intent provoker configured to provide rehabilitation-related sense, exercise and cognition information to a user to induce sense, exercise and cognition of the user; a biological signal detector configured to measure a biological signal of the user; a state estimator configured to receive the biological signal of the user from the biological signal detector to generate state information of the user on the basis of the biological signal; a stimulation exercise presenter configured to provide a stimulation or an exercise to the user on the basis of the state information of the user generated by the state estimator; a stimulation exercise adjuster configured to adjust the stimulation or exercise provided to the user when the user is performing rehabilitation training, on the basis of the state information of the user generated by the state estimator; and a rehabilitation motive activator configured to provide a user experience environment to the user which is performing the rehabilitation training, by using virtual reality or augmented reality.

In another general aspect, the rehabilitation intent provoker may provide rehabilitation-related exercise, sense or cognition information to the user with image, sound or tactile sense and the biological signal detector may measure the biological signal by using at least one of a central nervous system-related biological signal measuring method, a musculoskeletal system-related biological signal measuring method, and a sensory system-related biological signal measuring method.

In another general aspect, a rehabilitation training method includes: providing rehabilitation-related information to a user to stimulate a sense of the user; measuring a biological signal of the user; estimating a state of the user on the basis of the biological signal; providing a stimulation or an exercise to the user on the basis of information on the state of the user; continuously measuring the biological signal of the user and, when a change in the biological signal is sensed, adjusting the stimulation or exercise provided to the user; and providing a user experience environment to the user by using virtual reality.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Hereinafter, embodiments of the present invention will be described in detail with reference to the accompanying drawings.

Figure 1:
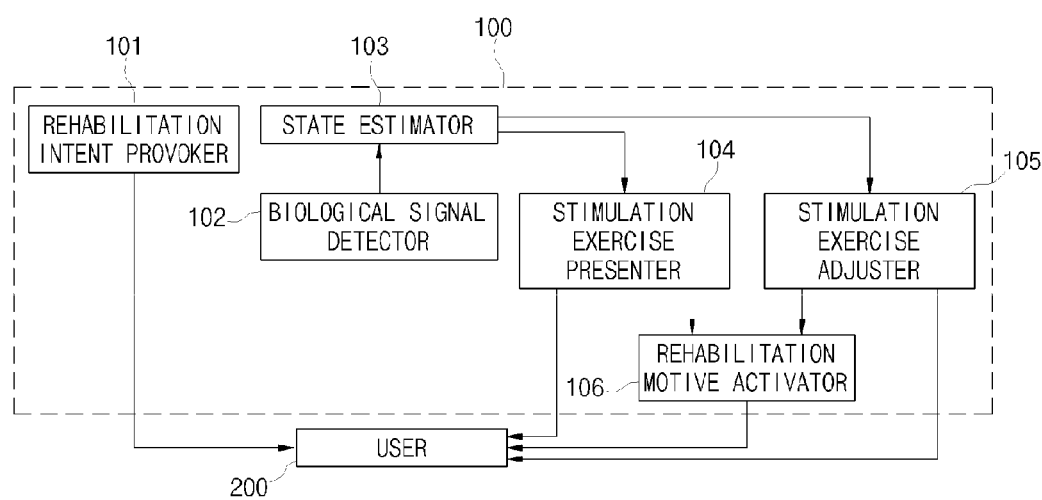
FIG. 1 is a block diagram illustrating a structure of a rehabilitation training system according to an embodiment of the present invention.

FIG. 1 is a block diagram illustrating a structure of a rehabilitation training system according to an embodiment of the present invention.

Referring to FIG. 1, a rehabilitation training system 100 according to an embodiment of the present invention includes a rehabilitation intent provoker 101, a biological signal detector 102, a state estimator 103, a stimulation exercise presenter 104, a stimulation exercise adjuster 105, and a rehabilitation motive activator 106.

The rehabilitation intent provoker 101 is for provoking a rehabilitation intent of a patient (user 200) depending on a rehabilitation part of the patient, and presents the patient with cognitive information such as imagination, memory, etc. associated with rehabilitation and sensory information such as observing, listening, touching, gesturing, smelling, tasting, etc, thereby provoking an intent to rehabilitate. The rehabilitation intent provoker 101 may use various means such as a screen, a perfume, a speaker, etc. for provoking the rehabilitation intent of the patient.

When a rehabilitation intent is presented or rehabilitation is performed, the biological signal detector 102 measures a state of the patient, and the state estimator 103 estimates the state of the patient.

The biological signal detector 102 is for detecting various body states of the patient when a rehabilitation intent of the patient is provoked by the rehabilitation intent provoker 101 or the patient is performing rehabilitation training, and may measure a biological signal of the patient by using a central nervous system-related biological signal measuring method such as electroencephalogram (EEG), magnetoencephalogram (MEG), functional near infrared spectroscopy (fNIRS), functional magnetic resonance imaging (fMRI), electrocorticogram (ECoG), or the like, a musculoskeletal system-related biological signal measuring method such as electromyograph (EMG), electrocardiogram (EKG), pulsimeter, goniometer, respirometer, accelerometer, or the like, or a sensory system-related biological signal measuring method such as electroretinogram (ERG), electrooculogram (EOG), galvanic skin response (GSR), electrocochleogram (ECoG), thermometer, manometer, or the like.

The state estimator 103 is for analyzing a biological signal measured by the biological signal detector 102 to estimate a state of the patient. The state estimator 103 refines the biological signal, extracts necessary features, and classifies the features to process the classified features into a suitable type of numerical values. In processing the features into the numerical values, various deterministic or statistical optimization techniques may be used.

Moreover, the biological signal detector 102 and the state estimator 103 may be divided into a rehabilitation intent extractor that detects a rehabilitation intent to estimate the state of the patient based on the rehabilitation intent when the rehabilitation intent is presented, and a rehabilitation state extractor that detects a biological signal of the patient based on rehabilitation to estimate a rehabilitation state of the patient when the patient is in rehabilitation.

The stimulation exercise presenter 104 is for providing a stimulation or an exercise to the patient according to the numerical values decided by the state estimator 103, and may provide a stimulation or an exercise to the patient by using a robot, such as a manipulator, a haptic device, a moving robot, or the like, and biological stimulation technology such as functional electrical stimulation (FES), transcranial direct current stimulation (tDCS), transcarnial magnetic stimulation (TMS), deep brain stimulation (DBS), magnetic resonance guided focused ultrasound (MRgFUS), or the like.

While the stimulation exercise presenter 104 provides a stimulation or exercise necessary for rehabilitation training to the patient, the stimulation exercise adjuster 105 adjusts the stimulation or exercise provided to the patient when a body state of the patient is changed by an intensity or continuous time of the rehabilitation training.

The stimulation exercise adjuster 105 continuously monitors the state of the patient through the biological signal detector 102 and the state estimator 103, and, when the state of the patient is changed, the stimulation exercise adjuster 105 adaptively decides the changed state to adjust the stimulation or exercise to a stimulation or exercise suitable for the continuously changing state of the patient.

The stimulation exercise adjuster 105 may use various control techniques such as optimal control, an observer, etc., and the stimulation or exercise adjusted by the stimulation exercise adjuster 105 may be immediately provided to the patient. However, the stimulation exercise adjuster 105 may command the stimulation exercise presenter 104 to provide a stimulation or exercise for adapting to the changed state, thereby adjusting the stimulation or exercise provided to the patient.

The rehabilitation motive activator 106 is for providing various user experience (UX) environments to the patient in order for the patient to concentrate on training and continue consistent training during the rehabilitation training, and can increase an efficiency of the rehabilitation training of the patient by using virtual reality, augmented reality, or the like for facilitating immersion, pleasure, desire to continue training, etc.

Figure 2:
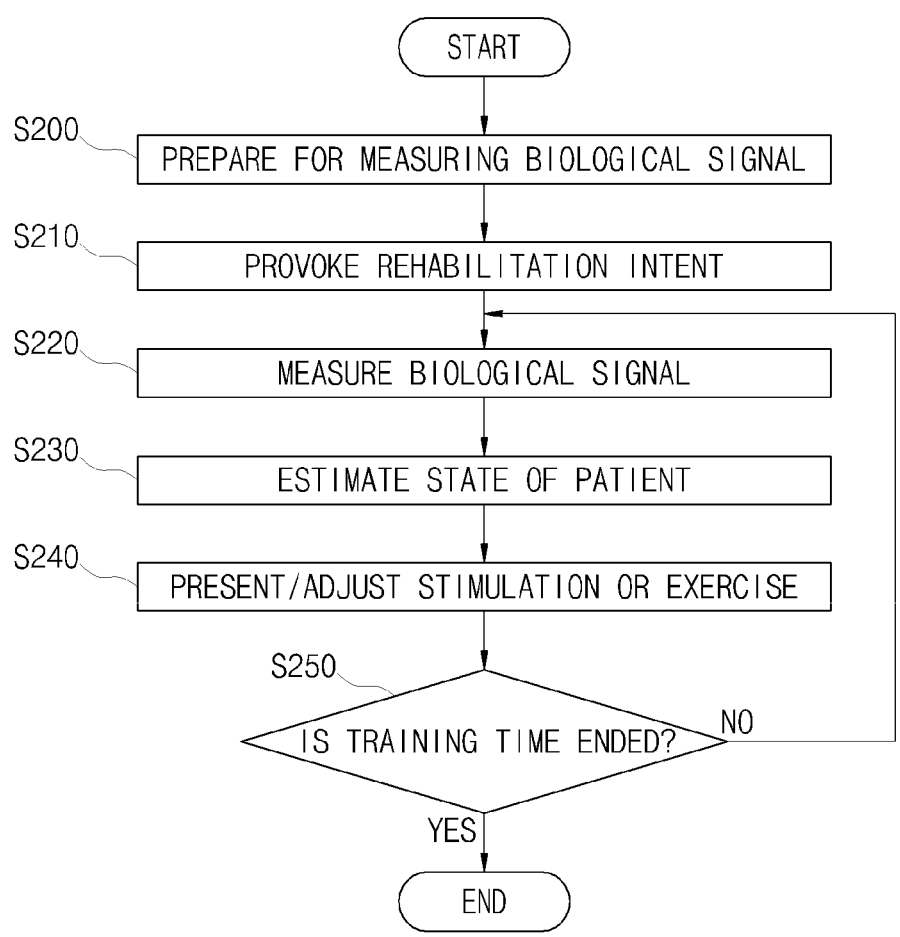
FIG. 2 is a flowchart illustrating a process of a rehabilitation training method according to an embodiment of the present invention.

FIG. 2 is a flowchart illustrating a process of a rehabilitation training method according to an embodiment of the present invention.

Referring to FIG. 2, before starting rehabilitation training, the rehabilitation training method prepares for measuring a biological signal of a patient, for measuring a state of the patient to provide effective rehabilitation training in operation S200. When the patient intends to start the rehabilitation training, the rehabilitation training method provides information, such as rehabilitation-related image, sound, etc., to the patient to provoke a rehabilitation intent of the patient in operation S210.

When the patient starts the rehabilitation training according to the rehabilitation intent being provoked, the rehabilitation training method measures a biological signal of the patient in operation S220, and analyzes the biological signal to estimate a state of the patient in operation S230.

In operation S240, the rehabilitation training method provides a stimulation or exercise necessary for rehabilitation of the patient to the patient, on the basis of the state of the patient which has been estimated based on the biological signal of the patient. Until the rehabilitation training of the patient is ended in operation S250, the rehabilitation training method continuously measures a biological signal of the patient in operation S220, and monitors a state of the patient in operation S230. When the state of the patient is changed, the rehabilitation training method adjusts the stimulation or exercise provided to the patient in operation S240.

Hereinafter, an embodiment to which the rehabilitation training method according to an embodiment of the present invention is applied will be described in detail.

A patient observes a rehabilitation exercise displayed on a screen, or imagines a rehabilitation exercise presented through a speaker or with voice of a therapist, according to predetermined rehabilitation guidelines. A brain cortex signal of the patient is measured by a noninvasive method in the fNIRS while provoking a rehabilitation intent, a current intent of the patient is extracted from the measured brain cortex signal, and a functional electrical stimulation suitable for the intent is applied to an appropriate rehabilitation part, thereby providing an active rehabilitation method enabling self-rehabilitation. At this time, a rehabilitation effect is changed to a numerical mark, and presented to the patient through a screen, thereby activating a rehabilitation motive of the patient. A muscular contraction of the patient may be measured by the EMG, and an intensity of a functional electrical stimulation may be adjusted to be suitable for a muscular activity based on rehabilitation.

A cap with a measurement probe stuck thereinto is worn by a scalp of the patient for measurement by the fNIRS, a patch is attached to skin of an appropriate rehabilitation part for applying a functional electrical stimulation, and a patch for measurement by the EMG is attached to a skin part close thereto.

The patient maintains a comfortable state, and a rehabilitation exercise is presented to the patient through a screen. The patient repeatedly observes or imagines the presented rehabilitation exercise for a certain time. The patient measures a hematocele metabolism of a brain cortex through the cap worn by the scalp by using the fNIRS.

Figure 3:
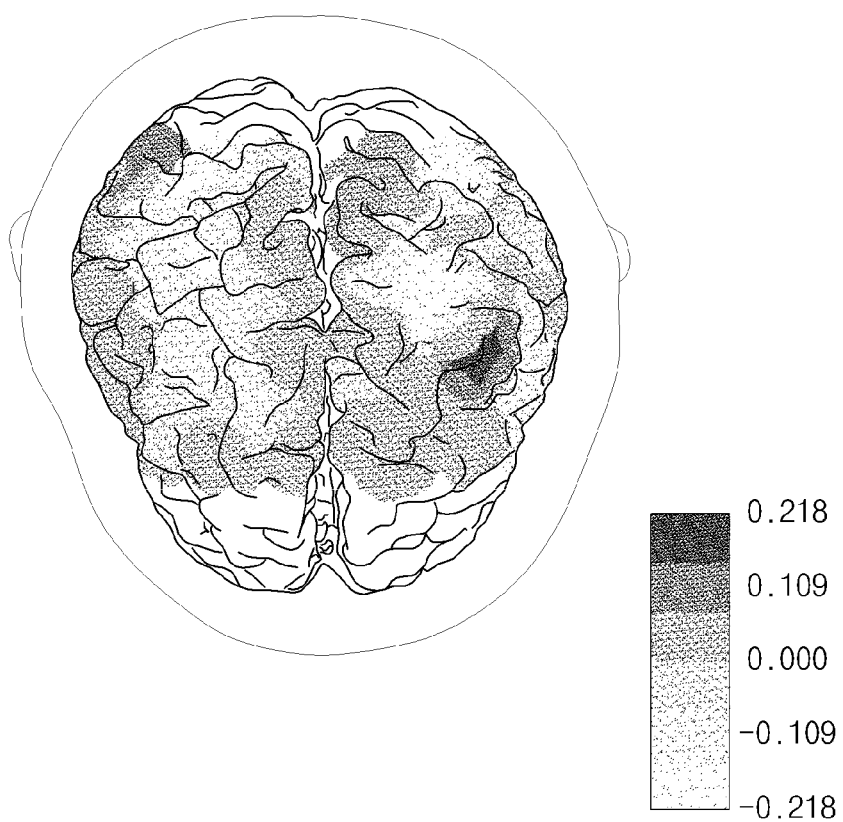
FIG. 3 is a diagram showing an embodiment of a monitoring screen provided to a user when the rehabilitation training system and method according to an embodiment of the present invention are carried out.

By measuring the hematocele metabolism of the brain cortex, as shown in FIG. 3, the patient may monitor an activity of the brain in the form of brain images displayed as numerals and colors. This denotes that as a numeral becomes larger, the frequency of activation is high. Accordingly, the patient can check brain activities by part with eyes while performing the rehabilitation training.

Figure 4:
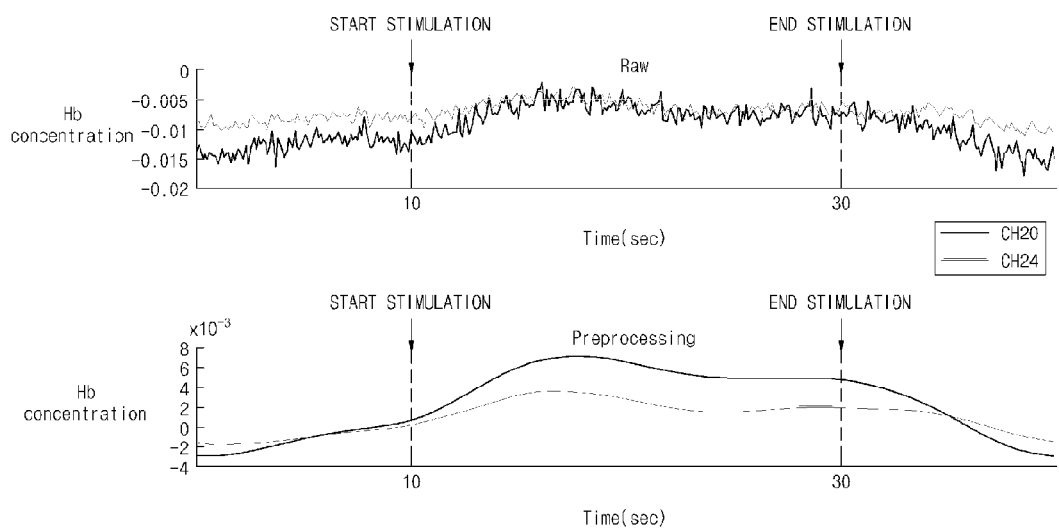
FIG. 4 is diagrams showing a signal, which measures a concentration of hemoglobin based on a hematocele metabolism, and a signal from which a noise is removed, when the rehabilitation training system and method according to an embodiment of the present invention are carried out.

A concentration of each of oxidized hemoglobin and non-oxidized hemoglobin based on the hematocele metabolism may be measured numerically, and a noise may be removed from the measured concentration signal through various pre-processing techniques. FIG. 4 partially shows the measured raw signal and the noise-removed signal.

A feature is extracted from the raw measurement signal or the noise-removed signal according to various learning techniques, and a rehabilitation intent is classified based on the extracted feature. A command for presenting a stimulation is generated by binarizing the rehabilitation intent.

A rehabilitation part of the patient moves by applying an intensity and time of a functional electrical stimulation in the maximum size allowable to the patient according to the binarized command. At this time, a muscular contraction of the patient is measured by the EMG, and when a muscular activity reaches a certain level, the intensity and time of the functional electrical stimulation may be gradually moderated. Also, a rehabilitation will of the patient is raised by displaying a recognition rate of the rehabilitation intent and a degree of muscular activity on a screen.

When a predetermined time elapses, rehabilitation training is ended according to rehabilitation guidelines provided by a doctor. Various equipment worn by the patient are removed from the patient, and standby is made for a certain time until the patient has a comfortable state. The rehabilitation training system explains and surveys the contents and result of the rehabilitation training to the patient, and then allows the patient itself to prepare for a rehabilitation training time.

As described above, the present invention enables a central nervous system damaged patent due to a brain damage or a spinal damage, a musculoskeletal disease patient, and a sports rehabilitation-requiring patient itself to actively train with motive and intent, thus effecting rehabilitation of the patients.

The present invention enables a patient to generate (feed-forward) an exercise order of a brain and feedback sensory information to activate a sensory-motor area of the brain through self-direction, and therefore enables the patient itself to carry out sensory-motor looped rehabilitation, thus separately or simultaneously enhancing a plasticity of brain, musculoskeletal recovery, and an exercise-enabling range.

According to the present invention, a patient can personally adjust an intensity and time of training depending on a state of the patient, thus effecting flexible rehabilitation training customized for the patient.

The present invention enables a patient to check an effect of its own rehabilitation training in real time, and easily provides a user experience environment suitable for the patient's preference to raise an immersion and motive of rehabilitation training, thus enhancing a result of the rehabilitation training.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A rehabilitation training system comprising:
a rehabilitation intent provoking device configured to provide rehabilitation-related sense, exercise or cognition information to a user to induce sense, exercise or cognition of the user before the user starts a rehabilitation training;
a biological signal detector configured to measure a first brain cortex signal of the user when the user starts the rehabilitation training according to the induced sense, exercise or cognition of the user;
a state estimator configured to receive the measured first brain cortex signal of the user from the biological signal detector to generate state information of the user on the basis of the measured first brain cortex signal;
a stimulation exercise presenter configured to automatically provide a stimulation or an exercise to the user on the basis of the state information of the user generated by the state estimator; and
a stimulation exercise adjuster configured to continuously monitor a state of the user on the basis of the generated state information of the user while the user is performing the rehabilitation training and to automatically adjust the stimulation or exercise provided to the user on the basis of the continuously monitored state of the user while the user is performing the rehabilitation training,
wherein the biological signal detector is further configured to measure a second brain cortex signal of the user responding to the provided stimulation or exercise, and an activity of the brain of the user based on the measured second brain cortex signal of the user is displayed on a screen, and
wherein the state estimator is further configured to automatically generate second state information of the user on the basis of the measured second brain cortex signal, and the stimulation exercise adjuster is further configured to automatically adjust the stimulation or exercise provided to the user based on the generated second state information of the user.

2. The rehabilitation training system of claim 1, wherein the rehabilitation intent provoking device provides the rehabilitation-related exercise, sense or cognition information to the user with image, sound or tactile sense.

3. The rehabilitation training system of claim 1, wherein the biological signal detector measures each of the first brain cortex signal and the second brain cortex signal of the user by using a central nervous system-related biological signal measuring method.

4. The rehabilitation training system of claim 1, further comprising a rehabilitation motive activator configured to provide a user experience environment to the user which is performing the rehabilitation training, by using virtual reality or augmented reality.

5. A rehabilitation training method comprising:
providing by a rehabilitation intent provoking device, rehabilitation-related information to a user to stimulate a sense of the user before the user starts a rehabilitation training;
measuring by a biological signal detector, a first brain cortex signal of the user when the user starts the rehabilitation training according to the stimulated sense of the user;
estimating by a state estimator, a state of the user on the basis of the measured first brain cortex signal;
automatically providing by a stimulation exercise presenter, a stimulation or an exercise to the user on the basis of information on the state of the user; and
continuously monitoring by a stimulation exercise adjuster, a state of the user based on the estimated state of the user while the user is performing the rehabilitation training, and automatically adjusting by the stimulation exercise adjuster, the stimulation or exercise provided to the user based on the continuously monitored state of the user while the user is performing the rehabilitation training,
wherein the method further comprises measuring by the biological signal detector, a second brain cortex signal of the user responding to the provided stimulation or exercise, automatically generating second state information of the user on the basis of the measured second brain cortex signal, and automatically adjusting the stimulation or exercise provided to the user based on the generated second state information of the user, and wherein an activity of the brain of the user based on the measured second brain cortex signal of the user is displayed on a screen.

6. The rehabilitation training method of claim 5, wherein when a change in the first brain cortex signal is sensed, the stimulation or exercise provided to the user is adjusted.

7. The rehabilitation training method of claim 5, further comprising providing a user experience environment to the user by using virtual reality.

* * * * *